United States Patent [19]

Osterried et al.

[11] Patent Number: 5,656,375
[45] Date of Patent: Aug. 12, 1997

[54] SURFACE-MODIFIED FLAKY SUBSTRATES HAVING IMPROVED SETTLING AND REDISPERSING CHARACTERISTICS

[75] Inventors: Karl Osterried, Dieburg; Gerhard Herget, Ober-Ramstadt; Ralf Glausch, Darmstadt; Roman Maisch, Rossdorf, all of Germany

[73] Assignee: Merck Patent Gesellschaft mit beschrankter Haftung, Darmstadt, Germany

[21] Appl. No.: 366,432

[22] Filed: Dec. 30, 1994

Related U.S. Application Data

[63] Continuation of Ser. No. 903,677, Jun. 24, 1992, abandoned

[30] Foreign Application Priority Data

Jun. 25, 1991 [DE] Germany .................. 41 20 921.4

[51] Int. Cl.⁶ .................................................. B32B 5/16
[52] U.S. Cl. .................. 428/403; 106/493; 106/494; 106/496; 428/407; 428/903
[58] Field of Search .................................. 428/403, 407, 428/363, 375, 378, 394, 903; 106/493, 494, 496

[56] References Cited

U.S. PATENT DOCUMENTS

| 4,544,415 | 10/1985 | Franz et al. ............ 428/405 X |
| 4,814,020 | 3/1989 | Kieser et al. ............ 428/363 X |
| 4,844,742 | 7/1989 | Jaffe ................... 524/87 X |
| 4,927,710 | 5/1990 | Tanaka et al. ............ 428/394 |
| 5,320,781 | 6/1994 | Stahlecker et al. ........ 252/518 |

FOREIGN PATENT DOCUMENTS 0198519  2/1985  European Pat. Off. .......... C09D 5/04

*Primary Examiner*—H. Thi Le
*Attorney, Agent, or Firm*—Millen, White, Zelano, & Branigan, P.C.

[57] ABSTRACT

The present invention relates to surface-modified pigments based on flaky substrates having improved settling and redispersing characteristics and to the preparation and use thereof.

10 Claims, No Drawings

SURFACE-MODIFIED FLAKY SUBSTRATES HAVING IMPROVED SETTLING AND REDISPERSING CHARACTERISTICS

This application is a continuation, of application Ser. No. 07/903,677, filed Jun. 24, 1992 now abandoned.

BACKGROUND OF THE INVENTION

The present invention relates to surface-modified pigments based on flaky substrates having improved settling and redispersing characteristics, and to the preparation and use thereof.

Coating compositions such as lacquers, paints, printing inks, etc., that contain pigments based on flaky substrates are problematical in handling in that the pigments, owing to their size and density, tend to settle out and can then become clumped together to form a very firm sediment cake. This cake is in general very difficult to redisperse. This is true in particular on storage of lathers, paints and printing inks and in the processing thereof.

As a consequence, numerous methods have been developed for solving the problem of incorporating and handling flaky pigments in coating compositions.

DE 36 27 329, EP 0 306 056 and EP 0 268 918 disclose that modified flaky substrates bearing a polymer coating or after treatment with coupling agents such as organotitanates and organosilanes show improved settling and redispersing characteristics in coating compositions.

Furthermore, redispersion can be facilitated by adding to the coating composition additives which bring about either a controlled flocculation (house of cards effect), a pseudoplastic and/or thixotropic response, steric hindrance and/or electrostatic repulsion of the pigments.

Additives which bring about thixotropy are described in EP-0 198 519 and DE-A-18 05 693. DE 39 22 178 discloses that mixing a suspension of a flaky substrate with spherical particles such as $SiO_2$, $TiO_2$ and $ZrO_2$ gives deagglomerated and readily dispersible pigments.

However, these additives can have a negative influence on the quality of the coating. Especially the brilliance of pearl luster (or "nacreous") pigments and the uniformity of the coating can be impaired. In general, the severity of these impairments increases with the concentration of the additives used.

SUMMARY OF THE INVENTION

It is an object of the present invention to find surface-modified pigments based on flaky substrates which on incorporation into a coating composition are free or substantially free of the disadvantages observed with conventional pigmented coating compositions.

It has now been found, surprisingly, that pigments which are based on flaky substrates and have been coated with a mixture comprising a binder, fibrous particles preferably having a fiber length of 0.1–20 μm and a solvent or solvent mixture show improved settling and redispersing characteristics in coating compositions.

The present invention accordingly provides surface-modified pigments which are based on a flaky substrate and which to improve the settling and redispersing characteristics have been coated with a modifying agent comprising a binder, fibrous particles preferably having a fiber length of 0.1–20 μm and a solvent or solvent mixture.

The present invention also provides a process for preparing surface-modified flaky substrates, characterized in that flaky substrates are coated with the modifying reagent comprising a binder, fibrous particles preferably having a fiber length of 0.1–20 m and a solvent or solvent mixture in a mixing vessel.

All known flaky metals, metal oxides, mica pigments and other flaky substrates can be coated by the process of the present invention.

Examples thereof are mica, talc, kaolin or other similar minerals and also flaky iron oxide and bismuth oxychloride.

Since the process does not require high shearing forces, it is also highly suitable for coating pearl luster.

All customary pearl luster pigments can be used, for example mica coatings with colored or colorless metal oxides, such as $TiO_2$, $Fe_2O_3$, $SnO_2$, $Cr_2O_3$, ZnO and other metal oxides, alone or mixed in a single layer or in successive layers. These pigments are known for example from German Patents and Patent Applications 14 67 468, 19 59 998, 20 09 566, 22 14 545, 22 15 191, 22 44 298, 23 13 331, 25 22 572, 31 37 808, 31 37 809, 31 51 343, 31 51 354, 31 51 355, 32 11 602 and 32 35 017 and are commercially available, for example from E. Merck, Darmstadt, under the trade name Iriodin®.

It is also surprising to observe that the coated substrates do not deteriorate in their optical properties. The concentration of modifying agent used can be 0.1–100% by weight, based on the pigment, but preferably it is 0.2–50%, in particular 0.5–20%.

The solvent used can remain on the pigment, in which case the pigments present in the preparation do not dust, or it can be removed after the coating process.

An essential constituent of the modifying agent are fibrous particles which are present in the modifying agent in an amount of about 0.1 to 100% by weight, in particular 1 to 50% by weight, preferably 5 to 20% by weight. The presence of these bulky particles prevents the substrates coated by the process of the present invention from becoming superposed to any significant extent owing to steric hindrance and hence prevents the particles from experiencing strong adhesion. The result is that the coated substrates will in some cases settle very much more slowly in lacquer and paint systems, but that in all cases the sediment will be less hard, and that there will be no problems with redispersing the sediment.

All organic and inorganic fibers 0.1–20 μm in length known to the person skilled in the art can be used. Suitable particles are in particular all synthetic fibers, for example polyethylene, polyacrylates, polypropylene, polyamides, cellulose fibers, inorganic fibers of which preferably silicon compounds, glass fibers and also in particular the condensation products of modified isocyanates and mono- and diamines.

These condensation products, which are diurea and its derivatives and also aminoureas having urethane groupings, are known as thixotropic agents and are added together with a binder to paints and lacquers in order to improve the run-off properties and the brushability. The coating of flaky substrates with a modifying agent containing a thixotropic agent has not been disclosed before.

The modifying agent used can be any diurea derivative and urethane compound known to the person skilled in the art, as described for example in EP 0 198 519, DE 18 05 693.4 and Organic Coatings: Science and Technology, A. Heenriga, P. J. G. von Hemsbergen, p. 201–222, New York 1983.

A further constituent of the modifying agent is a binder, which is present in the modifying agent in an amount of about 0 to 90% by weight, in particular about 20 to 50% by weight. It is possible to use any known polymer resin which has groups with an affinity for pigments and which has a molecular weight of 100–100,000, preferably 200–10,000, in particular 500–5,000, e.g. alkyl, acrylic, alkyd, acrylate resins, polyesters and mixtures of a plurality of polymer resins.

The process of the present invention is simple and easy to carry out. The pigment product is prepared by mixing the active substances mentioned in a solvent. For this it is possible to use any organic solvent, e.g. esters, acetates, alcohols such as ethanol, propanol isopropanol, methoxypropanol, tert-butanol, and also aromatic solvents, e.g. benzene, xylene, in particular toluene. The modifying agent is characterised in that it contains 0 to 90% by weight, preferably 5 to 80% by weight, in particular 10 to 70% by weight, of solvent or solvent mixture.

The modifying agent is applied to the pigment by simply mixing with the substrate, for example in a tumbler, propeller wheel, paddle or fluid mixer, of which, on account of the relatively high frangibility of the substrates, slow-speed mixers are preferred. Since high shearing forces are not necessary in preparing the pigment product, the process of the present invention is also highly suitable for pearl luster pigments.

The pigment product of the present invention is compatible with a large number of color systems, especially in the area of lacquers, paints and printing inks.

The present invention thus also provides for the use of the coated substrates in formulations such as paints, printing inks, lacquers and for cosmetic products.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire disclosures of all applications, patents and publications, cited above and below, and of corresponding application German P 41 20 921.4, filed Jun. 25, 1991, are hereby incorporated by reference.

EXAMPLES

I. Tests of the settling and redispersing characteristics of the pigment preparations in printing inks Example 1

A mixing vessel with a propeller wheel stirrer is charged with 200 g of Iriodin 100 (TiO$_2$-mica having a particle size of 1–60 m from E. Merck, Darmstadt) which is admixed with a mixture of 20 g of Setal® 90173 SS-50 (available from AKZ0) in 40 g of 1-methoxy-2-propanol (Setal® is a modifying agent consisting of a diurea derivative, polyester resin, xylene, Solvesso® 100 from Synthese, Boxmer, and also 1-methoxy-2-propanol) over a period of 5 minutes by stirring.

The result is a nondusting pigment preparation having excellent redispersing characteristics, Example 2

Example 1 is repeated, except that Iriodin 300 (Fe$_2$O$_3$/TiO$_2$-mica having a particle size of 10–60 m from E. Merck, Darmstadt) is coated with 20 g of Setal.

Example 3

Example 1 is repeated, except that Iriodin 300 (Fe$_2$O$_3$-mica having a particle size of 10–60 μm from E. Merck, Darmstadt) is coated with 20 g of Setal.

Example 4a

Example 1 is repeated, except that Iriodin 225 (TiO$_2$-mica having a particle size of 10–60 μm from E. Merck, Darmstadt) is coated with 20 g of Setal.

Example 4b

Example 1 is repeated, except that 200 g of Iriodin 225 are introduced as .initial charge and admixed with 10 g of Setal.

Example 4c

Exmnple 1 is repeated, except that 200 g of Iriodin 225 are introduced as initial charge and admixed with 5 g of Setal.

Example 5

45 g of a commercially available nitrocellulose combination blend from Huber München, Kirchheim-Heimstetten, are admixed with 15 g of Iriodin 100 a little at a time by stirring with a vane stirrer. A 1:1 mixture of ethyl acetate/ethanol was used to set an efflux time of 17 sec (DIN 4 cup).

Example 6

Example 5 was repeated, except that 45 g of the nitrocellulose combination blend were admixed with 19.5 g of Iriodin preparation (Example 1) a little at a time by stirring. A 1:1 mixture of ethyl acetate/ethanol was used to set an efflux time of 17 sec.

Example 7

Settling and Redispersing Experiments 50 ml at a time of the pigmented printing inks of Examples 5 and 6 are introduced into a graduated cylinder. The sediment volume is determined over 30 days. Using a special measuring mandrel the penetration depth is determined on day 30 in relation to the total sediment height. The depth of penetration is a measure of the firmness of the sediment and is inversely proportional thereto.

TABLE

| | Sediment volume (ml) | | | | | | penetration depth/ sediment height (mm/mm) |
|---|---|---|---|---|---|---|---|
| | 1 | 2 | 5 | 24 days | 48 | 30 | |
| Example 5 | — | 47.5 | 45 | 17 | 17 | 13.2 | 15/35 |
| Example 6 | — | 49 | 46.5 | 30.2 | 27.5 | 19 | 51/51 |

Intaglio handprinted samples with the two printing inks do not differ in gloss.

Example 8

45 g of a commercially available printing ink based on nitrocellulose from-Hartmann, Frankfurt, were admixed with 15 g of Iriodin 100 or 300 or 500 by stirring. 1:1 ethyl acetate/ethanol was used to set 18 sec DIN 4 cup.

Example 9

45 g of a commercially available printing ink based on nitrocellulose from Hartmann, Frankfurt, were admixed with 19.5 g of pigment preparation from Example 1, Example 2 or Example 3. Ethyl acetate/ethanol was used to set 18 sec DIN 4 cup.

Example 10

Settling and Redispersing Experiments According to Example 7

|  | Sediment volume (ml) after standing time (h) |  |  |  |  | Penetration depth/ sediment height (mm/mm) |
|---|---|---|---|---|---|---|
|  | 1 | 5 | 24 days | 4 | 40 |  |
| Example 8 (Iriodin 100) | 49 | 40 | 24 | 24.2 | 20 | 54*/54 |
| Example 1 | 4.8 | 40.2 | 35.2 | 34 | 29 | 78/78 |
| Example 8 (Iriodin 300) | 49.8 | 40 | 20.5 | 20.8 | 16 | 25/43 |
| Example 1 | 48 | 48 | 26 | 25.5 | 23.2 | 62*/62 |
| Example 8 (Iriodin 500) | 48.5 | 41.5 | 23.5 | 23.8 | 19 | 51*/51 |
| Example 1 | 49.5 | 46.5 | 31 | 28 | 25.8 | 69/69 |

*The mandrel descends slowly to the bottom.

The intaglio handprinted samples with all three printing inks containing the Iriodin preparation were as brilliant as the comparative samples.

Example 11

45 g at a time of a nitrocellulose blend (consisting of 9.62% of nitrocellulose, 3.85% of hard resin and 86.53% of ethanol; solids content=13.46%) were admixed a little at a time with 15 g of Iriodin 225 or 19.5 g of preparation 4a), or 17.3 g of preparation 4b), or 16.1 g of preparation 4c), by stirring with a blade stirrer. 1-Methoxy-2-propanol was used to set 16 sec DIN 4 cup.

Example 12

Settling and redispersing experiments according to Example 7

TABLE

|  | Sediment volume (ml) after standing time (h) |  |  |  |  | Penetration depth/ sediment height (mm/mm) |
|---|---|---|---|---|---|---|
| Example 11 | 2 | 8 | 24 days | 4 | 8 |  |
| Iriodin 225 | 45 | 30 | 10 | 10 | 10 | 7/27 |
| Preparation 2.5% of modifying agent | 40 | 18 | 11 | 11 | 11 | 8/29 |
| Preparation 5% of modifying agent | 40 | 15 | 14 | 14 | 14 | 37/37 |
| Preparation 10% of modifying agent: | 41.8 | 24 | 20 | 20 | 20 | 53/53 |

II. Investigation of settling and redispersing characteristics of pigment preparations in lacquers 2.1 Procedure The pigment is modified and incorporated into various lacquer systems. The entire batch is introduced into a 50 ml graduated cylinder to a depth of 30 ml and the sediment formed by the pigment is recorded at weekly intervals in ml.

2.2 Lacquer batches a) Comparative batch

In the comparative batch, 5% of uncoated substrate based on the entire lacquer formulation are incorporated into various laquer systems and the settling characteristics are determined.

b) Addition of additives to lacquer

The batch is prepared as described under a), 10% of Setal based on the pigment weight are added to the lacquer system, and the settling characteristics are determined.

c) Addition of the modified pigment

The pigment according to the present invention is incorporated into the lacquer system as described under a) and the settling characteristics are determined.

2.3 Results a) Settling characteristics

TABLE 1

Pigment: Iriodin 9103 (TiO$_2$-mica having a particle size of 10–40 µm from E. Merck, Darmstadt)
Additive: Setal 90173 SS-50

| Pigment height (ml) Batch (lacquer) | Time (d) | | | | | | | | |
|---|---|---|---|---|---|---|---|---|---|
|  | 7 | 14 | 21 | 28 | 35 | 42 | 49 | 56 | 63 |
| a) Single-coat acrylic-melamine (lacquer system 1) | 1 | 1 | 1 | 1 | 0.5 | 0.5 | 0.5 | 0.5 | 0.5 |
| b) Single-coat acrylic-melamine (lacquer system 1) | 2 | 2 | 2 | 2 | 1.4 | 1.4 | 1.4 | 1.4 | 1.4 |
| c) Single-coat acrylic-melamine (lacquer system 1) | 4.8 | 3.4 | 3 | 3 | 3 | 3 | 3 | 3 | 3 |
| a) Two-coat low solids acrylic-melamine (lacquer system 2) | 26 | 19.5 | 16 | 14 | 13 | 12.5 | 12 | 11.5 | 11.5 |
| b) Two-coat low solids acrylic-melamine (lacquer system 2) | 26.5 | 23 | 20.5 | 18 | 16 | 15 | 13.5 | 13 | 13 |
| c) Two-coat low solids acrylic-melamine (lacquer system 2) | 27 | 24 | 21 | 18 | 16.7 | 15 | 13.5 | 13 | 13 |
| a) Two-coat high solids acrylic-melamine (lacquer system 3) | 19.5 | 14.5 | 13 | 12.5 | 12.5 | 12 | 12 | 12 | 12 |

TABLE 1-continued

Pigment: Iriodin 9103 (TiO$_2$-mica having a particle size of 10–40 µm from E. Merck, Darmstadt)
Additive: Setal 90173 SS-50

| Pigment height (ml) Batch (lacquer) | Time (d) | | | | | | | | |
|---|---|---|---|---|---|---|---|---|---|
| | 7 | 14 | 21 | 28 | 35 | 42 | 49 | 56 | 63 |
| b) Two-coat high solids acrylic-melamine (lacquer system 3) | 23 | 15.5 | 13.5 | 12.5 | 12 | 12 | 12 | 12 | 12 |
| c) Two-coat high solids acrylic-melamine (lacquer system 3) | 27 | 21 | 17 | 15 | 14 | 13.5 | 13.5 | 13.5 | 13.5 |

As is evident from Table 1, the pigment height is in every case greatest with batches c), i.e. the pigments do not settle out to such an extent as those of a) and b).

Similar results were obtained with Iriodin 504 (Fe$_2$O$_3$-mica having a particle size of 10–60 µm from E. Merck, Darmstadt).

b) Redispersibility of sediment

TABLE 2

Redispersibility of sediments of Iriodin 9103 in lacquer batches a), b) and c)

| Lacquer system, lacquer batch | Single-coat acrylic-melamine (lacquer system 1) | Low-solids acrylic-melamine (lacquer system 2) | High-solids acrylic-melamine (lacquer system 3) |
|---|---|---|---|
| a) | very firm sediment clumping redisperses only on prolonged stirring | very readily redispersible | very readily redispersible |
| b) | very readily redispersible, somewhat worse than c) | very readily redispersible | very readily redispersible |
| c) | very readily redispersible | very readily redispersible | very readily redispersible |

As in 3a, lacquer batch c) is always most readily redispersible.

c) Gloss measurement

The effect of the organic coating on the gloss was measured (gloss measurement system after Erichsen) and no significant influence was found in the case of the two two-coat systems (lacquer systems 2+3). In the single-coat system (lacquer system 1) it was found that the organic coating resulted in an increase in gloss.

TABLE 3

| Lacquer system | Lacquer batches (see 2.2.) | Erichsen |
|---|---|---|
| Single-coat Acrylic-melamine (lacquer system 1) | a) | 18 |
| | b) | 35 |
| | c) | 59 |
| Two-coat Low solids Acrylic-melamine (lacquer system 2) | a) | 98 |
| | b) | 97 |
| | c) | 95 |
| Two-coat High solids | a) | 93 |
| | b) | 95 |

TABLE 3-continued

| Lacquer system | Lacquer batches (see 2.2.) | Erichsen |
|---|---|---|
| Acrylic-melamine (lacquer system 3) | c) | 94 |

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A surface-modified pigment comprising a platelet-shaped substrate coated with a modifying agent comprising fibrous particles and a polymeric binder, whereby the settling and redispersing characteristics have been improved compared to a non-surface-modified pigment.

2. A surface-modified pigment according to claim 1, wherein the modifying agent further comprises an organic solvent or solvent mixture.

3. A surface-modified pigment according to claim 2, wherein the solvent is an aromatic solvent, an alcohol, an alkyl acetate or a mixture thereof.

4. A surface-modified pigment according to claim 1, wherein the fibrous particles have a fiber length of about 0.1–20 µm.

5. A surface-modified pigment according to claim 1, wherein the fibrous particles are synthetic fibers, inorganic fibers, or cellulose fibers.

6. A surface-modified pigment according to claim 1, wherein the binder is a polymer resin.

7. A surface-modified pigment according to claim 1, wherein the substrate is a nacreous pigment.

8. A surface-modified pigment according to claim 6, wherein the polymer resin has groups with an affinity for pigments and is an alkyl, acrylic, alkyd, acrylate or polyester resin, or a mixture thereof.

9. A surface-modified pigment according to claim 1, wherein the fibrous particles are diureas or aminoureas.

10. A surface-modified pigment according to claim 9, wherein the fibrous particles are diureas or aminoureas having urethane groups.

* * * * *